United States Patent [19]

Kenda

[11] Patent Number: 4,495,951
[45] Date of Patent: Jan. 29, 1985

[54] APPARATUS FOR SEPARATELY CATCHING SUCCESSIVE STREAMS OF URINE AT TAKING SAMPLES TO LABORATORIAL AND BACTERIOLOGICAL EXAMINATION

[76] Inventor: Rajko Kenda, Pražakova 6, 61000 Ljubljana, Yugoslavia

[21] Appl. No.: 311,316

[22] Filed: Oct. 14, 1981

[51] Int. Cl.³ .......................... A61F 5/44; A61M 1/00
[52] U.S. Cl. ..................................... 128/762; 604/317; 604/323; 4/144.3; 73/864.51
[58] Field of Search ............... 604/317, 318, 323, 324, 604/325, 326, 327, 329, 331; 128/760, 761, 762, 317, 318, 324, 327; 4/144.1, 144.2, 144.3, 144.4; 73/863.52, 864, 864.51

[56] References Cited

U.S. PATENT DOCUMENTS

| | | | |
|---|---|---|---|
| 2,674,265 | 4/1954 | Dennis | 73/864 X |
| 3,750,647 | 8/1973 | Gleason et al. | 604/329 |
| 3,943,770 | 3/1976 | McDonald | 73/863.52 |
| 4,040,791 | 8/1977 | Kuntz | 128/761 |
| 4,233,978 | 11/1980 | Hickey | 4/144.3 |
| 4,252,132 | 2/1981 | Kuntz | 128/761 |
| 4,276,889 | 7/1981 | Kuntz et al. | 128/761 |
| 4,331,162 | 5/1982 | Kuntz et al. | 128/761 |

OTHER PUBLICATIONS

Czech Magazine "Cs.Pediat", 1977, xxxii year, pp. 226–228, vol. 4 by D. Krema.

Primary Examiner—C. Fred Rosenbaum
Assistant Examiner—J. L. Kruter
Attorney, Agent, or Firm—Fleit, Jacobson, Cohn & Price

[57] ABSTRACT

Apparatus used with a seated patient for separately catching successive streams of urine for taking samples for laboratorial and bacteriological examination. The apparatus enables an automatic separation of initial, median, and final streams caught in a vessel. The vessel also is used to transport the sample from the patient to a laboratory.

3 Claims, 1 Drawing Figure

U.S. Patent Jan. 29, 1985 4,495,951
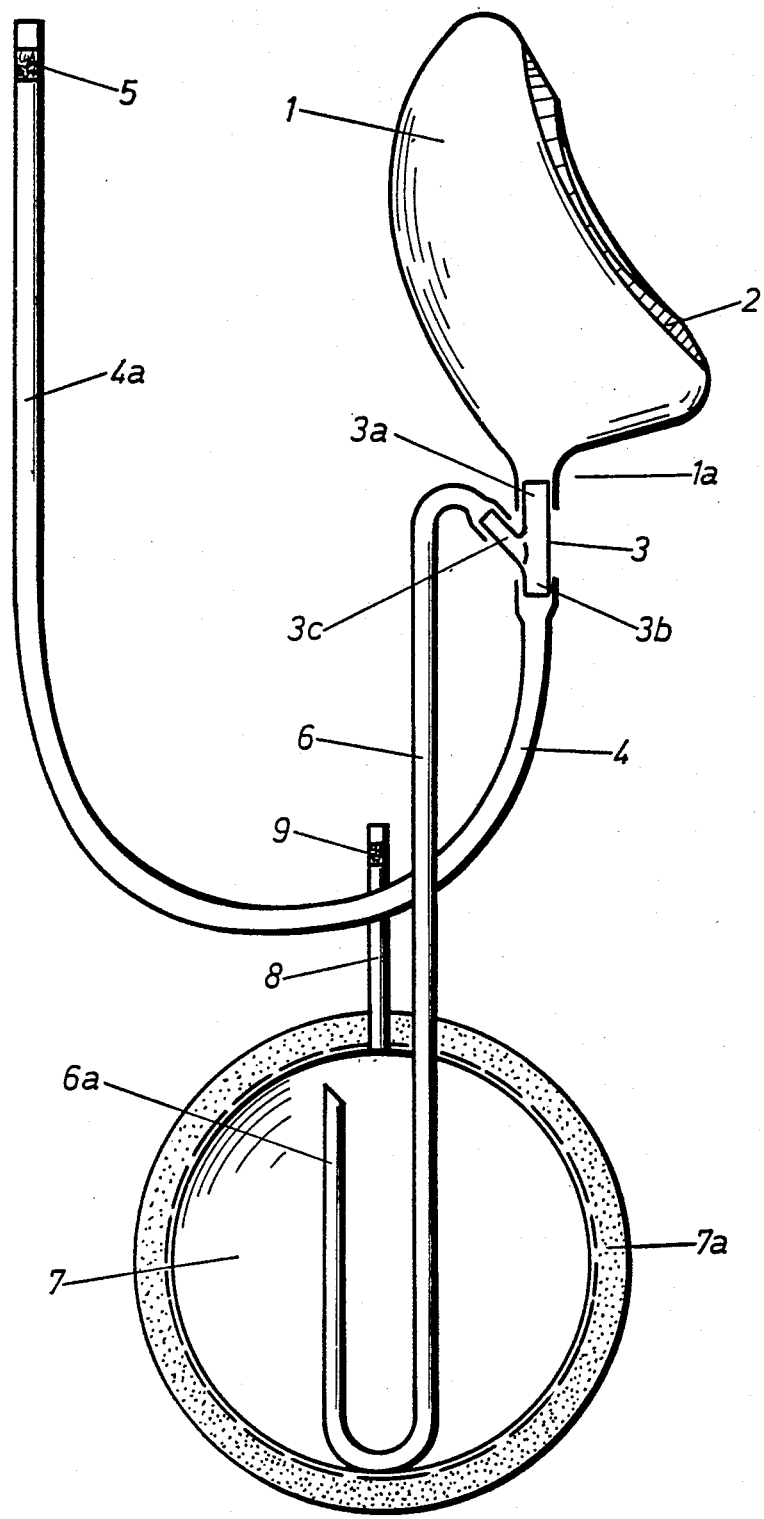

APPARATUS FOR SEPARATELY CATCHING SUCCESSIVE STREAMS OF URINE AT TAKING SAMPLES TO LABORATORIAL AND BACTERIOLOGICAL EXAMINATION

BACKGROUND OF THE INVENTION

1. Field of the Invention

The present invention relates to an apparatus for separately catching successive streams of urine for taking samples for laboratorial and bacteriological examination, and more concretely, to a single-use apparatus adapted for newborns and small children, as well as adults, who, owing to whatever hindrances, cannot cooperate with the examiner. The proposed apparatus is applied with the seated patient in a seat position.

The objective of the bacteriological examination of urine is to obtain information on the number and species of bacteria in urine from the bladder and the upper parts of the urinary tract, respectively. Further therapy, hospitalization, and diagnostic procedures are dependent on said information. Each false-positive result is of course unacceptable to the patient, who will be unnecessarily submitted to diagnostic and therapeutic treatment. Additionally, such false-positive results will cause superfluous costs either to the medical institution or the patient himself.

Said false-positive results and contamination, respectively, of an urine sample are due to several causes, the most important of them are: the urethra is populated by bacteria which, when urinating, mix with the caught urine, so that the findings lead to the impression that an infection were in question; the same false impression exerted by fecal contamination and a contamination from the perigenital region, respectively; and the sample being further contaminated when decanting the urine from the collector into a vessel in which the urine will be transported to the laboratory.

2. Description of the Prior Art

From the Czech magazine "Čs.Pediat.", 1977, xxxii year, page 226, vol. 4, there is known an apparatus (by D. Krčma) designated as midstream urine collector for newborns and nurslings. In this apparatus there runs, from an adapter sticked around the genitalia of the lying patient, a long flexible pipe extending beyond the border of the bed which has its free end inserted through a stopper of a free-hinged test-tube. From the hinged section, i.e. vertical section, of this flexible pipe a branch pipe, immediately above the test tube, is led slopingly upwards, provided with a further flexible pipe which is shorter than the first one and, like the first pipe, terminates in its own hinging test-tube. In addition to said two flexible pipes there is foreseen a small ventilating pipe in each stopper.

When applying said known apparatus there have to be selected, according to the available disclosure, two test-tubes of an appropriate size wherein some oil is dropped which later on floats on the urine, and after an adequate viscosity has been selected, closes the ventilating pipes when both test-tubes are filled up. When catching urine, this apparatus is applied as follows: when voiding, first the adapter and then the section of the first flexible pipe resting on the bed are filled up, and thereupon the test-tube of the first pipe becomes full. The urine which is left over is diverted at the aforementioned branch pipe and streams into the second test-tube. Presumably, the second test-tube is great enough to accumulate the whole of the left-over urine.

According to the concept of the Czech inventor, the urine in question, kept in the second test-tube, is separated from the presumably contaminated urine kept in the first test tube. However, the analysis of the disclosed situation shows the following.

First, the conception of the apparatus as such, according to which the adapter is filled up with the urine which comes into contact with the skin, makes it possible to contaminate the urine; the proportionally long section of the first flexible pipe becomes contaminated with the first, i.e. polluted, stream of the urine and as such injuriously influences the left-over stream. Second, the preparation of this apparatus for the application is a time-consuming task due to the insertion of the necessary oil. And third, the entire manipulation with the apparatus, particularly the insertion of oil as well as the oil as such involves additional contamination of the sample and the interior of the apparatus, respectively.

Beside the above-mentioned "constructional" disadvantages attention should be drawn also to the following. It can be anticipated that the last section of the urine stream, i.e. approximately 2 cc urine, containing liquid particles from the wrinkles of the bladder wall, is more densely populated by the bacteria than the left-over urine contents of the bladder. However, said last stream cannot be separated by the known apparatus.

SUMMARY OF THE INVENTION

From the aforesaid circumstances there proceeds the fundamental object of the invention, namely, to deliver to the laboratory a sample of urine which will reflect the real status of the urine in the patient's bladder.

When selecting the way to attain the proposed aim I proceeded from the usual manner of taking samples from the adults, where the first stream of the urine washing off the urethra is thrown away, and for the examination the next stream is caught. When manipulating newborns and small children, who urinate randomly, the urine will of course be caught by an appropriate apparatus.

A further object of the invention, i.e. one proceeding from the above analysis, is to eliminate the disadvantages as mentioned above and to create an improved apparatus which will enable a separate accumulation of the first, the median and the last stream of urine, respectively.

These and other objects to be exposed in the following detailed description can be realized by using a special chair, which is not an object of the present patent application, in which the patient on whom the proposed apparatus is arranged is comfortably seated, as well as by using an apparatus constructed as described in the examples and defined in the corresponding patent claims.

BRIEF DESCRIPTION OF THE DRAWINGS

The embodiment of the invention will now be described with reference to the pertinent drawing showing a preferred single variant embodying the invention as proposed.

DESCRIPTION OF THE PREFERRED EMBODIMENT

In the drawing an adapter 1 with a self-sealing strip 2 is shown in a side elevational view; it is adapted to be fastened onto the sitting patient and provided with a adapter outlet 1a located at the lowest position. From below a connecting piece 3 is inserted into said adapter outlet 1a, comprising two coaxial connectors 3a, 3b, and an inclined, upwardly directed branch 3c. The diameter of the branch 3c is preferably smaller than the diameters of the connectors 3a, 3b which are preferably equal to each other. To the lower connector 3b a flexible pipe 4 is connected the free end 4a of which is bent vertically so that its top lies above the adapter 1 or at the highest on the same level. The free end 4a of the pipe 4 is preferably stopped by a wadding 5. To the branch 3c there is connected a further flexible pipe 6 which is freely suspended and comprises an upwardly directed free end 6a. The lower section of said pipe 6 with the appertaining free end 6a is inserted into an accumulating vessel 7 which is provided with a ventilating pipe 8. Also said pipe 8 is preferably but not necessarily stopped up by a wadding 9.

In the embodiment as disclosed there is used an accumulating vessel 7 consisting of two hemispherical shells of transparent plastic, having a jointing ring 7a, wherein the vertical pipe 6 and the ventilating pipe 8 are fixed. With respect to the scope of manufacturing, various design modifications of the accumulating vessel are possible. However, it is preferably to apply plastics.

The apparatus is sterilized in packed form together with an appropriate hermetically closed package which is not presented in the drawing.

After the patient—to say, a nursling—has been placed onto the special chair and fixed by his legs in the region above the knees, and has been made clean, the apparatus is taken from the package, the security foil removed from the self-sealing strip 2 and the apparatus arranged by adjusting the adapter 1 around the genitalia. Hereafter, only the vertical section 4a of the pipe 4 has to be fixed at an adequate level onto the chair, and the apparatus is thus completely prepared for use.

When urinating, the urine passes without retention directly into the coaxial flexible pipe 4 of the adapter 1. If in the further description the dynamic properties of the fluid were neglected and a simplified interpretation were sufficient, the following could be stated. After the level of the urine in the free end 4a has reached the level of the connecting piece 3 (a little higher, in fact), the stream of the urine is diverted through the branch 3c to the pipe 6 where it leaves the free end 6a and accumulates within the vessel 7, the air leaving through the ventilating pipe 8. It is foreseen that the vessel 7 should never be filled up. If a greater quantity of urine is to be expected, it is possible to lower the section 4a of the pipe 4 to thereby catch more urine into said pipe. Therefore, the pipe 4 also serves as a control means.

It follows from the above description that the initial, i.e. the first stream of the urine is caught in the pipe 4, the midstream in the vessel 7, and the last stream of the urine left in the lower U-bend of the pipe 6. All of the urine has left the adapter 1; consequently, the patient remains dry.

Samples of urine as such can be obtained in several ways:

in dependence upon the construction of the apparatus;

in dependence upon the one or more successive streams which is to be examined. At all events, it is recommended that a part or parts of the proposed apparatus wherein urine has been caught can serve as a transporting means.

If it proves necessary to separate the whole of urine only into the initial and the final stream (the midstream being combined), the direct pipe is omitted, the second pipe 6 is displaced from its original branch 3c to the lower connector 3b, and the branch 3c is stopped.

What I claim is:

1. Apparatus for separately catching and retaining successive parts of a stream of urine for taking samples for laboratorial and bacteriological examination, said apparatus adapted for use with a seated patient and comprising:

adapter means for catching a stream of urine and including an adapter outlet;

separating means for automatic separation of the initial, the medial and the final (approximately 2 cc) parts of the urine stream that is caught, said separating means including a first chamber means for receiving and retaining an initial part of the urine stream and accumulating vessel means for receiving and collecting a medial part of the urine stream, flexible tube means providing communication between said adapter means and said accumulating vessel means, said medial stream passing directly from said adapter means through said flexible tube means to said accumulating vessel, said flexible tube means comprising a flexible tube having an upwardly directed free end extending within said accumulating vessel and another end connected to the adapter outlet by an upwardly inclined branch of a connecting piece positioned between said adapter means and said first chamber means, said flexible tube means also serving to receive and retain the final part of the urine stream; and said accumulating vessel means for receiving and retaining the medial part of the urine stream serving as a transporting means between the patient and a laboratory.

2. Apparatus for separately catching successive streams of urine for taking samples for laboratorial and bacteriological examination, applied with a seated patient, and for automatic separation of the initial, the medial, and the final (approximately 2 cc) streams of urine caught into a vessel means intended to serve as a transporting means between the patient and a laboratory, said apparatus comprising:

an adapter for receiving the urine, said adapter provided with a self-sealing strip;

a connector including a coaxial branch connected to said adapter and an inclined upwardly directed branch extending laterally with respect to the adapter;

a first flexible pipe connected to one end of said coaxial branch of said connector, said pipe bent in a U-form with its free end placed above the level of the connector; and a second flexible pipe connected to said upwardly directed branch and extending downwardly to a second flexible pipe and including a free end that is upwardly oriented an end section of said second pipe together with the upwardly oriented free end thereof defining a loop; and a closed accumulating vessel provided with a ventilating pipe, said loop of said second pipe positioned within said vessel.

3. An apparatus for catching a stream of urine and for separating the stream into initial, medial, and final portions, said apparatus comprising:

an adapter for receiving a stream of urine from a patient, the adapter having an outlet in a lowermost portion thereof;

a connecting piece extending from said outlet, said connecting piece having upper and lower coaxial portions and an inclined, upwardly directed branch having an upper end and a lower end, said lower end in fluid communication with at least one of said coaxial portions;

a first pipe means having a first end connected to a lower end of the lower coaxial portion of said connecting piece and a second end means positionable at a level higher than the level of the outlet of said adapter;

a second pipe means having a first end connected to said upper end of said inclined upwardly directed branch of said connecting piece and a second end extending into an accumulating vessel; and a closed vessel for accumulating a medial portion of the stream of urine, said second pipe means extending within said vessel and defining a substantially U-shaped loop with the second end of said second pipe means being upwardly directed in said vessel so that the initial portion of a stream of urine enters and fills the first pipe means to prevent flow through said lower portion of said coaxial means and a medial portion of the stream flows into said upwardly directed branch and into said second pipe means to enter said vessel, the final portion of the stream remaining within said second pipe means.

* * * * *